US009655630B2

(12) United States Patent
Hernandez et al.

(10) Patent No.: US 9,655,630 B2
(45) Date of Patent: May 23, 2017

(54) METHODS AND DEVICES FOR FORMING HOLES IN BONE TO STIMULATE BONE GROWTH

(71) Applicant: DePuy Mitek, LLC, Raynham, MA (US)

(72) Inventors: Joseph Hernandez, Sandwich, MA (US); David B. Spenciner, North Attleboro, MA (US); Bethany F. Grant, Scituate, MA (US); Dina Belloli, Foxboro, MA (US); John R. Cournoyer, Norfolk, MA (US); Scott A. Woodruff, Boston, MA (US); Jonathan Correia, Boston, MA (US)

(73) Assignee: DEPUY MITEK, LLC, Raynham, MA (US)

( * ) Notice: Subject to any disclaimer, the term of this patent is extended or adjusted under 35 U.S.C. 154(b) by 0 days.

(21) Appl. No.: 14/965,428

(22) Filed: Dec. 10, 2015

(65) Prior Publication Data
US 2016/0095607 A1    Apr. 7, 2016

Related U.S. Application Data

(62) Division of application No. 13/756,084, filed on Jan. 31, 2013, now Pat. No. 9,237,894.

(51) Int. Cl.
*A61B 17/16*    (2006.01)
*A61B 17/56*    (2006.01)

(52) U.S. Cl.
CPC .......... *A61B 17/1604* (2013.01); *A61B 17/16* (2013.01); *A61B 17/1657* (2013.01); *A61B 17/56* (2013.01); *A61B 2017/564* (2013.01)

(58) Field of Classification Search
CPC . A61B 17/16; A61B 17/1604; A61B 17/1657; A61B 17/56; A61B 2017/564
See application file for complete search history.

(56) References Cited

U.S. PATENT DOCUMENTS

| 5,584,837 | A | 12/1996 | Petersen |
| 6,126,664 | A | 10/2000 | Troxell et al. |
| 6,143,012 | A | 11/2000 | Gausepohl |
| 6,423,073 | B2 | 7/2002 | Bowman |

(Continued)

FOREIGN PATENT DOCUMENTS

WO    WO 2013112308 A1 *    8/2013    ......... A61B 17/1604

OTHER PUBLICATIONS

U.S. Appl. No. 13/705,472, filed Dec. 5, 2012.

*Primary Examiner* — Larry E Waggle, Jr.

(57) ABSTRACT

Methods and devices are provided for forming holes in bone to stimulate bone growth. In one exemplary embodiment, a surgical instrument set can include a driver having a first mating element, and a bone pick have a second mating element configured to releasably mate with the first mating element at any of a plurality of angular orientations. When releasably mated together, the driver and the bone pick can be configured to be adjustably positioned relative to one another with three degrees of freedom, e.g., pitch, yaw, and roll. The bone pick can include a piercing tip configured to form a hole in a bone, such as in microfracture. When the driver and the bone pick are releasably mated together, the driver can be configured to be struck, impacted, or otherwise manipulated to drive the piercing tip into the bone.

6 Claims, 8 Drawing Sheets

(56) References Cited

U.S. PATENT DOCUMENTS

| | | |
|---|---|---|
| 7,335,207 B1 | 2/2008 | Smith |
| 7,942,881 B2 | 5/2011 | Torrie et al. |
| 9,237,894 B2 | 1/2016 | Hernandez et al. |
| 2010/0249786 A1 | 9/2010 | Schmieding et al. |
| 2011/0054537 A1 | 3/2011 | Miller et al. |
| 2011/0270308 A1* | 11/2011 | Kilburn-Peterson  A61B 17/0401 606/232 |
| 2014/0214039 A1 | 7/2014 | Hernandez et al. |

* cited by examiner

METHODS AND DEVICES FOR FORMING HOLES IN BONE TO STIMULATE BONE GROWTH

CROSS REFERENCE TO RELATED APPLICATIONS

This application is a divisional of U.S. application Ser. No. 13/756,084 filed Jan. 31, 2013, and entitled "Methods and Devices for Forming Holes in Bone to Stimulate Bone Growth," which is hereby incorporated by reference herein in its entirety

FIELD

The present disclosure relates generally to methods and devices for forming holes in bone to stimulate bone growth.

BACKGROUND

Cartilage on articular surfaces of bones at joints within a body provide important protection for the underlying bone. Portions of the bone supporting the articular cartilage are typically referred to as sub-chondral bone. Both acute and chronic injury of articular cartilage causes chondral defects, which can lead to progressive joint pain and impaired mobility.

Various remedies exist to address chondral defects, such as a surgical procedure including microfracture. Microfracture involves selective perforation of sub-chondral bone. Numerous studies show that microfracture beneath a chondral defect can result in a blood clot filling the chondral defect with pluripotent marrow-derived mesenchymal stem cells that produce beneficial fibrocartilage repair tissue.

In a microfracture procedure, a surgeon typically debrides unstable cartilage down to the sub-chondral bone layer to support subsequent basilar integration of the new repair tissue. Microfracture can be accomplished thereafter using one or more rigid, curved awls that are manually manipulated through arthroscopic access sheaths or cannulas, and sometimes struck with a mallet, to create a series of microfracture holes in sub-chondral bone. Working space at chondral defects is usually limited, and it is difficult to manipulate the awls effectively, especially within hip joints. A surgeon may need to exchange awls of different curvatures at different stages of the procedure, which can lengthen a time of the surgical procedure. Additionally, the cutting tips of the awls are exposed during insertion and withdrawal from the body as well as during use on bone, which can result in cuts and/or other damage to tissue and/or other material by which the awl passes during insertion and withdrawal. Skiving of the awl's tip across bone, for example, can cause longitudinal disruptions and potential weakening of sub-chondral bone.

Accordingly, there remains a need for improved methods and devices for forming holes in bone to stimulate bone growth.

SUMMARY

The present invention generally provides methods and devices for forming holes in bone to stimulate bone growth. In one aspect, a surgical instrument set is provided that includes a driver and a bone pick. The driver can have a first elongate shaft with a first mating element on a distal portion thereof. The bone pick can have a second elongate shaft with a second mating element on a distal portion thereof and can have a piercing tip formed on the distal portion thereof. The second mating element can be configured to releasably mate with the first mating element such that, when releasably mated, the driver is angularly adjustable relative to the bone pick.

The instrument set can vary in any number of ways. At least one of the driver and the bone pick can include a locking mechanism configured to lock the driver in a selected angular position relative to the bone pick when the first and second mating elements are releasably mated together. The piercing tip can extend from the distal portion of the bone pick at a non-adjustable angle. The bone pick can include an adjustment mechanism configured to adjust an angle at which the piercing tip extends from the distal portion of the bone pick. The first elongate shaft can be a solid member, or the first elongate shaft can be cannulated.

The first and second mating elements can have any number of variations. One of the first and second mating elements can include a ball, and another of the first and second mating elements can include a socket. When the second mating element is releasably mated with the first mating element, the first mating element can be configured to rotatably move relative to the second mating element, e.g., the first mating element can be configured to be manually rotated relative to the second mating element. The first and second mating elements can be releasably matable without being able to be locked in a fixed position relative to one another. The first and second mating elements can be releasably matable by snap fit. The first and second mating elements are configured to be releasably mated together within a body of a patient and to be unmated from one another within the body of the patient.

In another embodiment, a surgical instrument set is provided that includes a first elongate shaft and a second elongate shaft. The first elongate shaft can have a first mating element in a distal portion thereof. The distal portion of the first elongate shaft and a distal portion of the second elongate shaft being configured to be advanced into a body. The second elongate shaft can have a piercing tip extending from a distal portion thereof. The piercing tip can be configured to penetrate into bone. The second elongate shaft can have a second mating element in the distal portion of the second elongate shaft. The first mating element can be configured to be releasably mated with the second mating element in the body at a plurality of orientations such that the first elongate shaft can extend at variable angles relative to the second elongate shaft. The surgical instrument set can optionally include a locking mechanism configured to lock the first elongate shaft at a selected one of the angles relative to the second elongate shaft when the first and second mating elements are releasably mated together.

In another aspect, a surgical method is provided that includes advancing an elongate shaft of a first surgical tool into a body of a patient and advancing a second surgical tool into the body of the patient. The second surgical tool can include a piercing tip in a distal portion thereof. The surgical method can also include releasably mating the first and second surgical tools together in the body of the patient, and, with the first and second surgical tools releasably mated together, adjusting an angle of the elongate shaft relative to the piercing tip. With the elongate shaft at the selected angle, a force can be applied to the first surgical tool, thereby causing the piercing tip to pierce a hole in a bone of the patient.

The surgical method can vary in any number of ways. Advancing the first surgical tool into the body of the patient can include advancing the first surgical tool through a first portal providing access into the body of the patient, and advancing the second surgical tool into the body of the patient can include advancing the second surgical tool through a second portal providing access into the body of the patient. Adjusting the angle of the elongate shaft relative to the piercing tip can include adjusting a longitudinal axis of the elongate shaft to be substantially perpendicular to a surface of the bone and to be non-parallel to a longitudinal axis of the piercing tip, the force being applied to the first portion of the surgical tool when the longitudinal axis of the elongate shaft is substantially perpendicular to the surface of the bone and is non-parallel to the longitudinal axis of the piercing tip. Releasably mating the first and second surgical tools together can include mating a first mating element on a distal portion of the elongate shaft with a second mating element on a distal portion of the second surgical tool. The surgical method can include releasing the first surgical tool from the second surgical tool in the body of the patient, and, after releasing the first surgical tool from the second surgical tool in the body of the patient, removing the first surgical tool from the body of the patient and removing the second surgical tool from the body of the patient. The surgical method can include releasing the first surgical tool from the second surgical tool in the body of the patient, and, after releasing the first surgical tool from the second surgical tool in the body of the patient, advancing a surgical instrument through an inner passageway extending through the elongate shaft such that a distal end of the surgical instrument advances toward the bone.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various methods and devices are provided for forming holes in bone to stimulate bone growth. In one exemplary embodiment, a surgical instrument set can include a driver having a first mating element, and a bone pick have a second mating element configured to releasably mate with the first mating element at any of a plurality of angular orientations. When releasably mated together, the driver and the bone pick can be configured to be adjustably positioned relative to one another with three degrees of freedom, e.g., pitch, yaw, and roll. In other words, the driver and the bone pick can be configured to be polyaxially positioned relative to one another. The bone pick can include a piercing tip configured to form a hole in a bone, such as in microfracture. When the driver and the bone pick are releasably mated together, the driver can be configured to be struck, impacted, or otherwise manipulated to drive the piercing tip into the bone. The force applied to the driver can be transferred to the bone pick in a direction substantially perpendicular to a surface of the bone, which can help reduce chances of the piercing tip accidentally slipping and gouging soft tissue and/or the bone in an unintended location. The driver and the bone pick can be independent members configured to be separately advanced into a body and releasably mated together within the body. The plurality of possible angular orientations of the driver and the bone pick can allow the driver and the bone pick to be advanced into the body through different access portals while still allowing the driver and the bone pick to releasably mate together within the body such that the driver can impart a force to the bone pick to drive the piercing tip into the bone. The plurality of possible angular orientations of the driver and the bone pick relative to one another can allow one or both of the different access portals to be access portals previously used, and/or to be subsequently used, in the same surgical procedure in which the piercing tip is being used to pierce bone. This availability of portals can ease performance of the surgical procedure and help reduce a number of patient incisions. The plurality of possible angular orientations of the driver and the bone pick can facilitate use of the surgical instrument set in various anatomical locations, e.g., hip, knee, shoulder, etc., and with a variety of differently sized patients because the surgical instrument set does not require a particular angular approach to a surgical site since the driver and the bone pick can be mated together within a patient's body at any of a plurality of angles. The variable angular orientations of the driver and the bone pick relative to one another can facilitate access of constrained joints, such as a hip joint, that are typically difficult to access at different angles without damaging cartilage and/or adjacent bone. The driver can be cannulated such that before and/or after the piercing tip has pierced the bone, one or more surgical instruments can be advanced through the cannulated interior of the driver. The driver can thus help reduce a number of devices needed to perform a surgical procedure and can help reduce tissue trauma because fewer access devices through which surgical instruments can be advanced into the body need be inserted and removed from the patient. The cannulated interior can facilitate advancement of the driver into the body over a guidewire.

The surgical devices disclosed herein can be used in a variety of surgical procedures. In an exemplary embodiment, the surgical device can be used in a surgical procedure involving microfracture on a hip, a knee, a shoulder, or other anatomical structure. The devices disclosed herein can be particularly effective in performing microfracture at a hip because, as mentioned above, the hip is a constrained joint that is typically difficult to access. A person skilled in the art will appreciate that the devices disclosed herein can be used in a variety of other medical procedures in which a hole is formed in bone.

The surgical devices disclosed herein can be formed from a variety of materials. A driver and a bone pick can each be formed of one or more materials, same or different from one another. In an exemplary embodiment, the driver and the bone pick can be made from one or more surgically safe, rigid, metal material(s), e.g., stainless steel, titanium, etc. A person skilled in the art will appreciate that a variety of other materials, such as ceramics and plastics, can be used to form the first and second portions of the device. In an exemplary embodiment, at least a piercing tip of the bone pick can be formed of rigid material(s), which can facilitate penetration of the piercing tip into bone and help prevent the piercing tip from deforming or flexing when penetrating into the bone.

Figure 1:
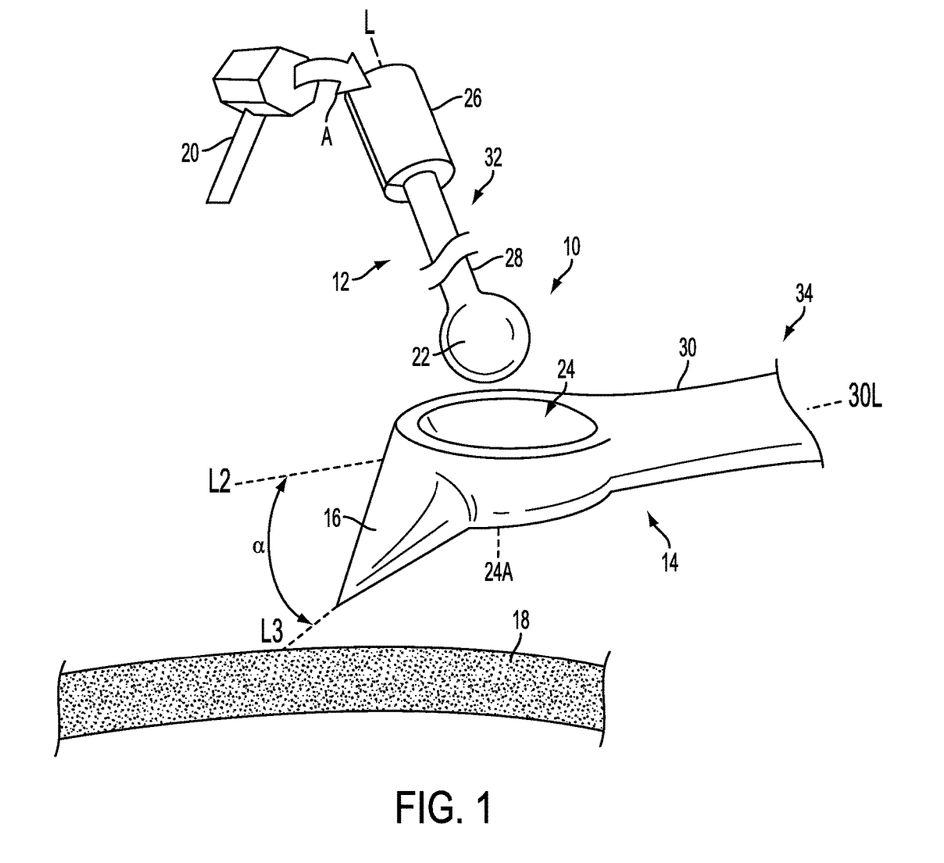
FIG. 1 is a perspective view of one embodiment of a surgical instrument set including a driver and a bone pick, and a mallet configured to provided a distally directed force to a proximal end of the driver, the driver and the bone pick being in an unmated configuration.

FIG. 1 illustrates one exemplary embodiment of a surgical instrument set 10 including a driver 12 and a bone pick 14 configured to releasably mate with the driver 12. The bone pick can include a piercing tip 16 configured to form a hole (not shown) in a bone 18. When the driver 12 and the bone pick 14 are releasably mated together, the driver 12 can be configured to be struck, impacted, or otherwise manipulated, e.g., by being struck by a mallet 20 as shown by arrow A, to impart a force to the bone pick 14 and thereby drive the piercing tip 16 into the bone 18. The driver 12 can be struck, impacted, or otherwise manipulated any number of times to form a single hole in the bone 18 and can be struck, impacted, or otherwise manipulated any number of times to cause the piercing tip 16 to form any number of holes in the bone 18, as appropriate for a particular surgical procedure.

Figure 2:
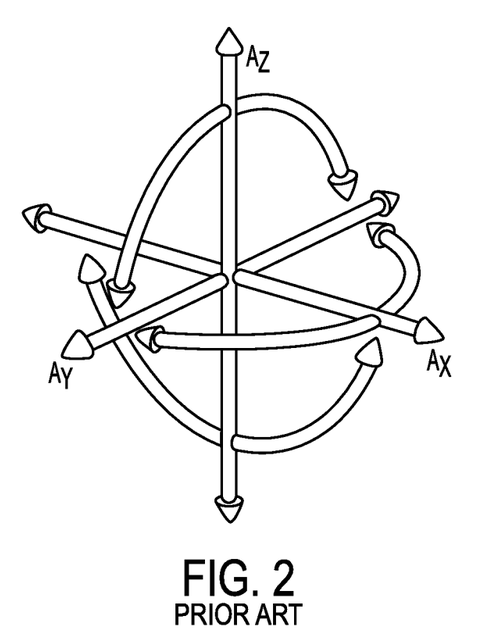
FIG. 2 (PRIOR ART) is a coordinate scale showing roll, yaw, and pitch rotation.

When the driver 12 and the bone pick 14 are releasably mated together, the driver 12 and the bone pick 14 can be polyaxially adjustable. In other words, the driver 12 and the bone pick 14 can be angularly adjusted relative to one another with at least three degrees of freedom, e.g., pitch P about a Y axis $A_Y$, yaw Y about a Z axis $A_Z$, and roll R about an X axis $A_X$, as shown in FIG. 2. The driver 12 and the bone pick 14 can be configured to releasably mate together in a variety of ways. The driver 12 can include a first mating element 22 formed thereon and configured to releasably mate with a second mating element 24 formed on the bone pick 14.

The first and second mating elements 22, 24 can have a variety of sizes, shapes, and configurations. The first and second mating elements 22, 24 can include complementary male and female elements configured to movably mate together. As in the illustrated embodiment, the first mating element 22 can include a male element, e.g., a convex element such as a ball, and the second mating element 24 can include female element, e.g., a concave surface such as a socket, configured to movably seat the male element therein. The convex element can include a recessed spherical surface and the concave element can include a corresponding protruding spherical surface. The first and second mating elements 22, 24 can thus be configured to mate together without any locking connection therebetween. In other words, the first and second mating elements 22, 24 can be configured to releasably mate together without being able to be locked in a fixed position relative to one another. Such a matable connection without locking can facilitate quick mating of the first and second mating elements 22, 24 within a body, can allow the first and second mating elements 22, 24 to be unmated within a body with substantially no removal force that could cause the driver 12 and/or the bone pick 14 to be jarred into adjacent tissue and/or other structure and cause damage thereto, and/or can simplify manufacture of the driver 12 and the bone pick 14. In another embodiment, the convex element can have a different rounded shape, such as a cone shape having a rounded end. Although the driver 12 includes a male element and the bone pick 14 includes a mating element in the illustrated embodiment, the mating elements can be reversed. Namely, a driver can include a female mating element, e.g., include a concave surface, and a bone pick can include a male mating element, e.g., include a convex surface.

The first and second mating elements 22, 24 can optionally include complementary guide features (not shown) configured to guide the first and second mating elements 22, 24 together into mated engagement. In an exemplary embodiments, the guide features can include one or more magnets in each of the driver 12 and the bone pick 14, e.g., magnets embedded with the driver 12 and the bone pick 14 within or adjacent to the first and second mating elements 22, 24 thereof. The magnets can help draw the first and second mating elements 22, 24 into mated engagement while still allowing the driver 12 and the bone pick 14 to be angularly adjusted relative to one another while in mated engagement via the first and second mating elements 22, 24.

The driver 12 can have a variety of sizes, shapes, and configurations. The driver 12 can be a solid member, as in the illustrated embodiment. Alternatively, a driver can be cannulated, e.g., have at least one longitudinal passageway extending therethrough, such that one or more surgical instruments can be advanced through the cannulated interior of the driver. The cannulated interior can allow the driver to be advanced into a body over a guidewire extending through the passageway and/or allow one or more surgical instruments to be advanced through the driver before and/or after the driver has mated to a bone pick and imparted a force thereto so as to drive a piercing tip of the bone pick into bone. For non-limiting example, a scoping device, as will be appreciated by a person skilled in the art, including a camera can be advanced through the passageway to provide visualization of a surgical site. For another non-limiting example, a suction device, as will also be appreciated by a person skilled in the art, can be advanced through the passageway after the bone pick has formed one or more holes in bone such that the suction device can suction away bone debris. For yet another non-limiting example, a beneficial substance, e.g., irrigation fluid, anti-bacterial fluid, adhesive gel, etc., can be introduced to a surgical site by being injected through the passageway, as will also be appreciated by a person skilled in the art.

Referring again to the embodiment of FIG. 1, the driver 12 can include an elongate shaft 28 having the first mating element 22 formed in a distal portion of the shaft 28 and having a handle 26 formed in a proximal portion of the shaft 28. The shaft 28 can have a cylindrical shape and a substantially circular cross-sectional shape, as in the illustrated embodiment. The shaft 28 can have other shapes and cross-sectional shapes, as will be appreciated by a person skilled in the art, such as having an elliptical or a hexagonal cross-sectional shape.

As in the illustrated embodiment, the first mating element 22 can be located at a distal-most end of the driver 12, which can facilitate engagement of the first mating element 22 with the second mating element 24 when the first and second mating elements 22, 24 are being mated within a body, as discussed further below.

The handle 26 formed in the proximal portion of the shaft 28 can have a variety of sizes, shapes, and configurations, as will be appreciated by a person skilled in the art. The handle 26 can be configured to be manually manipulated, e.g., held by hand, outside a body of a patient. As in the illustrated embodiment, the handle 26 can have a cylindrical shape that extends distally from a proximal-most end of the driver 12. In an exemplary embodiment, a proximal-most end of the handle 26, and hence the proximal-most end of the driver 12, can have a substantially flat surface configured to be struck by the mallet 20 so as to provide a load or a driving force to the bone pick 14. The driver 12 can thus be configured to be struck at the proximal-most end thereof, which can help more evenly distribute force through the driver 12 than if the driver were struck at some intermediate portion that is distal to the proximal-most end of the driver 12. By being configured to be struck at a proximal-most end thereof, the driver 12 can be configured to be struck in a direction parallel to a longitudinal axis L thereof. The strike force can thus be directed directly toward the bone 18, thereby providing a relatively precise and predictable impact point of the piercing tip 16 into the bone 18. The strike force being directed directly toward the bone 18 can also reduce chances of the striking force causing the piercing tip 16 to skive across the bone 18 and/or be jarred into and damage cartilage or other soft tissue adjacent to the bone 18. The force applied to the driver 12 can be directed substantially perpendicular toward a surface of the bone 18 when the driver 12 is struck by the mallet 20, which can allow the striking force to be directed substantially perpendicular to the surface of the bone 18, which, similar to that discussed above, can provide a relatively precise and predictable impact point of the piercing tip 16 into the bone 18 and can reduce chances of the striking force causing the piercing tip 16 to skive across the bone 18 and/or be jarred into and damage cartilage or other soft tissue adjacent to the bone 18. The force can be directed substantially perpendicular toward a surface of the bone 18 because the force can be centrally applied to the second mating element 24, e.g., applied along a central axis 24A of the second mating element. The force applied perpendicular toward the surface of the bone 18 can reduce from 100% when the piercing tip 16 is aligned with a longitudinal axis of an impact handle, e.g., the longitudinal axis L of the driver 12, to 0% when the piercing tip 16 is 90° from the longitudinal axis of the impact handle. When the strike force can be aligned closer to the direction of the piercing tip 16, which generally wants to be perpendicular to the surface of the bone 18, the resulting applied force can be proportional to the cosine of the angle from the axis of the impact handle (strike force) to a longitudinal axis of the piercing tip 16 (piercing or applied force). For non-limiting example, when the piercing tip 16 is 30° from the longitudinal axis of the impact handle, 87% of the load can be transmitted in the piercing direction. The driver 12 and the bone pick 14 can thus allow close alignment of the piercing tip 16 and the driver 12.

The mallet 20 can have a variety of sizes, shapes, and configurations, as will be appreciated by a person skilled in the art. A non-limiting example of a mallet is the RigidFix® mallet available from Depuy Mitek of Raynham, Mass. As mentioned above, although the mallet 20 is shown in FIG. 1 with the instrument set 10, the driver 12 can be struck, impacted, or otherwise manipulated with a device other than the mallet 20 to provide the force to the bone pick 14, such as by being hit with a hammer or being manually pushed distally by hand. As will also be appreciated by a person skilled in the art, depending on a hardness of the bone 18, manually pushing the driver 12 by hand may not provide sufficient force for the piercing tip 16 to pierce the bone 18. A relatively large strike force is needed to pierce into most bone on which microfracture or other intentional piercing is performed.

The bone pick 14 can have a variety of sizes, shapes, and configurations. The bone pick 14 can include an elongate shaft 30 having the second mating element 24 and the piercing tip 16 formed in a distal portion of the shaft 30 and having a handle (not shown) formed in a proximal portion of the shaft 30. The shaft 30 can have a cylindrical shape and a substantially circular cross-sectional shape, as in the illustrated embodiment. The shaft 30 can have other shapes and cross-sectional shapes, as will be appreciated by a person skilled in the art, such as having an elliptical or a hexagonal cross-sectional shape. The shaft 30 in the illustrated embodiment is straight, but a shaft of a bone pick can be curved. Having a curved bone pick shaft can facilitate accessing a tight surgical space, such as a hip joint. Additionally, although the shaft 30 in the illustrated embodiment is rigid, a shaft of a bone pick can be flexible. A flexible bone pick shaft can facilitate positioning of the bone pick's piercing tip at a surgical site.

The shaft 30 can be a solid member, as in the illustrated embodiment. Alternatively, a shaft of a bone pick can be cannulated, similar to that discussed above regarding a passageway extending through a driver. A passageway extending through the bone pick's shaft can be in communication with a passageway extending through the bone pick's piercing tip, e.g., the bone pick can have a single passageway extending therethrough, such that the piercing tip is cannulated. The shaft's passageway and the bone pick's passageway can be in communication without communicating with the bone pick's mating element, e.g., without passing through a socket of the bone pick. If, instead, the shaft's passageway and the bone pick's passageway are in communication with the bone pick's mating element, a driver configured to mate with the mating element can have a passageway extending therethrough, e.g., in a mating element in a distal portion thereof, such that the passageways of the bone pick's shaft and piercing tip can be in communication even when the driver is mated with the bone pick.

The handle formed in the proximal portion of the shaft 30 can have a variety of sizes, shapes, and configurations, as will be appreciated by a person skilled in the art. The handle can be configured to be manually manipulated, e.g., held by hand, outside a body of a patient.

The piercing tip 16 can have a variety of sizes, shapes, and configurations. In an exemplary embodiment, the piercing tip 16 can have a cone shape. As in the illustrated embodiment, the piercing tip 16 can be located at a distal-most end of the bone pick 14, which can facilitate penetration of the piercing tip 16, and not the driver 12 or other portions of the bone pick 14, into the bone 18, as discussed further below. The bone pick 14 can include one or more piercing tips. In an exemplary embodiment, the bone pick 14 includes a single piercing tip 16, which can facilitate insertion of the bone pick 14 into a small surgical space, e.g., at a hip joint, can allow the bone pick 14 to be used in a procedure in which only a single bone hole is formed, and/or can allow a surgeon to choose locations of and distances between bone holes formed in the same bone.

The piercing tip 16 can extend at any angle α relative to a longitudinal axis 30L of the bone pick's shaft 30. The angle α is fixed in the illustrated embodiment, but the angle α can be variable, as discussed further below. In an exemplary embodiment, the angle α can be greater than zero, e.g., a longitudinal axis L3 of the piercing tip 16 can be non-parallel or angularly offset from the longitudinal axis 30L of bone pick's shaft 30 in at least a distal portion thereof. The non-zero angle α can facilitate direction of the force from the driver 12 to the piercing tip 16 instead of to the bone pick's elongate shaft 30. The angle α can, as in the illustrated embodiment, be an acute angle less than 90°, although the angle α can be 90° or an obtuse angle greater than 90°. The second mating element 24 can be positioned along the longitudinal axis 30L of the bone pick's shaft 30 such that the piercing tip 16 can extend at the angle α from the second mating element 24, as in the illustrated embodiment. Thus, when the first and second mating elements 22, 24 are mated together and the driver 12 provides a force to the bone pick 14, e.g., by being struck by the mallet 20, the force can be directed toward the piercing tip 16 extending away from the second mating element 24.

Because the angular orientation of the driver 12 and the bone pick 14 relative to one another can be adjusted when the first and second mating element 22, 24 are mated together, the axes L, L3 of the driver 12 and the piercing tip 16 can be angularly adjusted relative to one another. The driver 12 can be struck by the mallet 20, or other member as discussed above, when the axes L, L3 of the driver 12 and the piercing tip 16 are at any angle relative to one another. With the piercing tip 16 extending at a non-zero angle α relative to the bone pick's shaft 30 and from the second mating element 24, as in the illustrated embodiment, the force imparted by the driver 12 to the bone pick 14 can be directed to the piercing tip 16 even if the longitudinal axis L of the driver 12 is not parallel to the longitudinal axis L3 of the piercing tip 16.

The driver 12 and the bone pick 14 can be independent elements, as shown in FIG. 1, such that the driver 12 and the bone pick 14 can each be advanced into a body separate from one another. The driver 12 and the bone pick 14 can thus be configured to be advanced into a body through first and second access portals 32, 34, e.g., through different incisions, different trocars, etc., and mated together in the body. The driver 12 and the bone pick 14 can be directly inserted through skin as shown in FIG. 1, or one or both of the driver 12 and the bone pick 14 can be advanced through an introducer device (not shown), e.g., a cannula, a trocar, etc., advanced through their respective portals 32, 34. The introducer devices used for each of the driver and the bone pick 14 can be the same or different from one another. In an exemplary embodiment, first and second introducer devices in the form of a cannula can be advanced through each of the first and second portals 32, 34, respectively, and the driver 12 and the bone pick 14 advanced through the cannulas toward the bone 18. The cannulas can have a variety of sizes, shapes, and configurations, as will be appreciated by a person skilled in the art. In an exemplary embodiment, the cannulas can each have a diameter of up to about 15 mm, e.g., a diameter of about 7.5 mm, in a range of about 10 to 15 mm, etc.

Because the driver 12 and the bone pick 14 can have any one of a plurality of angular orientations relative to one another, the driver 12 and the bone pick 14 can be at any of numerous different angular positions relative to one another when the driver 12 and the bone pick 14 are advanced into the body and then initially mated together. The driver 12 and the bone pick 14 can be advanced into the body simultaneously or sequentially. In an exemplary embodiment, the bone pick 14 can be advanced into a body before the driver 12, which can allow the piercing tip 16 to be positioned adjacent to a target piercing site prior to the driver 12 and the bone pick 14 being mated together. The driver 12 can then be manipulated to impart a force to the bone pick 14 shortly after the first and second mating elements 16, 18 are mated together. Depending on an angular approach of the driver 12 and the bone pick 14 within a body, the driver 12 and the bone pick 14 may not need to be angularly adjusted relative to one another within the body after being mated together and prior to the driver 12 being struck, impacted, or otherwise manipulated to impart a force to the bone pick 14.

Prior to the first and second mating elements 22, 24 being mated together, the driver 12 and the bone pick 14 can each be configured to move with six degrees of freedom, e.g., rotatable in pitch P, yaw Y, and roll R and movable along the Y axis $A_Y$, the Z axis $A_Z$, and the X axis $A_X$, shown in FIG. 2. Being movable in six degrees of freedom can facilitate separate advancement of the driver 12 and the bone pick 14 into a body and facilitate separate positioning of the driver 12 and the bone pick 14 relative to the bone 18. When the first and second mating elements 22, 24 are mated together, the driver 12 and the bone pick 14 can be configured to have relative motion in at least three degrees of freedom, as mentioned above, in any one or more of pitch P, yaw Y, and roll R. Depending on sizes of the first and second mating elements 22, 24 relative to one another, when the first and second mating elements 22, 24 are mated together, the driver 12 and the bone pick 14 can be configured to have relative motion in five degrees of freedom, e.g., in pitch P, yaw Y, roll R and along the Y axis $A_Y$ and the X axis $A_X$. In other words, if the ball 22 has a smaller radius than the socket 24, the ball 22 can move back and forth along the Y axis $A_Y$ and the X axis $A_X$ when mated to the socket 24 in addition to being rotatable about each of the Y axis $A_Y$ (pitch P), the Z axis $A_Z$ (yaw Y), and the X axis $A_X$ (roll R). In an exemplary embodiment, the ball 22 and the socket 24 have substantially equal radii, which can help prevent accidental slippage of the ball 22 within the socket 24 when the driver 12 including the ball 22 is struck. In other words, in an exemplary embodiment, when mated together, the driver 12 and the bone pick 14 can be configured to have relative motion in three degrees of freedom.

Figure 3:
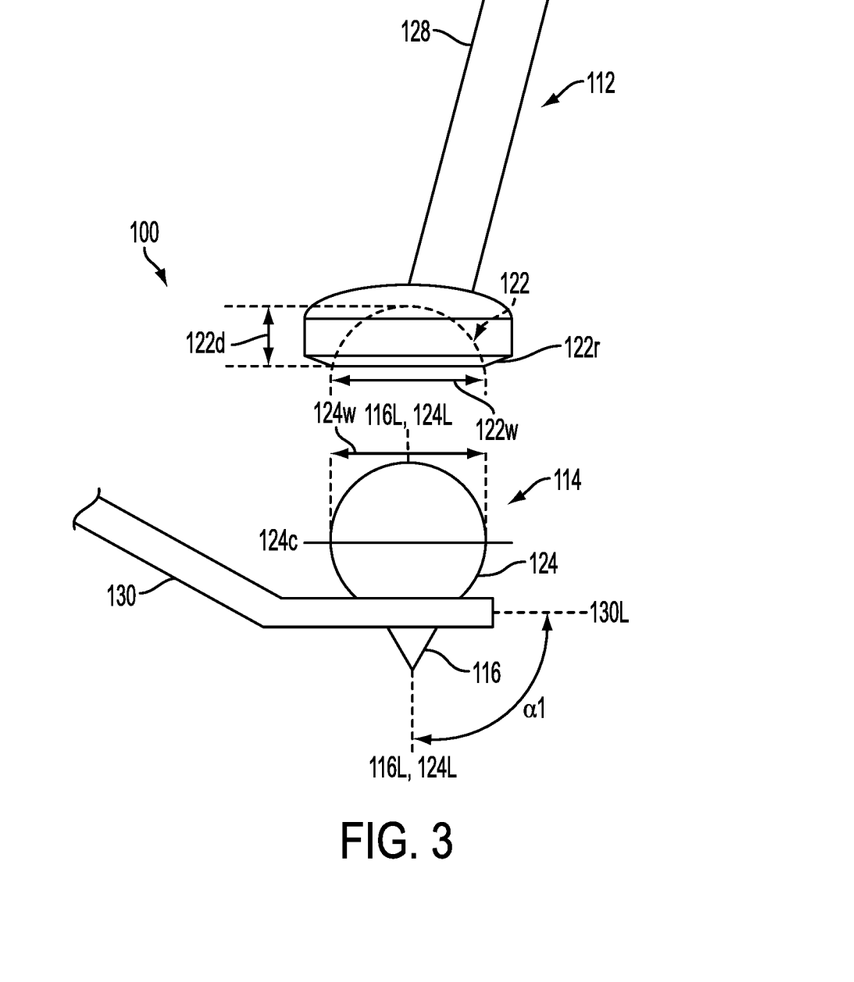
FIG. 3 is a side schematic view of another embodiment of a surgical instrument set including a driver and a bone pick, the driver and the bone pick being in an unmated configuration.
Figure 4:
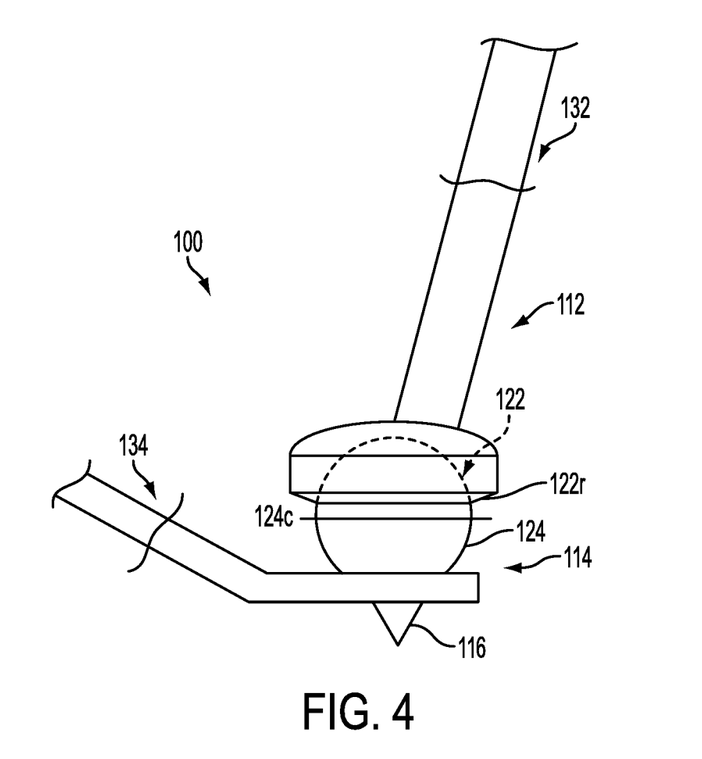
FIG. 4 is a side schematic view of the surgical instrument set of FIG. 3, the driver being advanced through a first access portal in a body, the bone pick being advanced through a second access portal in the body, and the driver and the bone pick being in a mated configuration.

FIGS. 3 and 4 illustrate another embodiment of a surgical instrument set 100 including a driver 112 and a bone pick 114 configured to releasably mate with the driver 112. The surgical instrument set 100 can generally be configured and used similar to the surgical instrument set 10 of FIG. 1, as the various embodiments of surgical instruments sets described herein can be configured and used similar to one another. The driver 112 and the bone pick 114 can be separate elements configured to be advanced into a body through first and second access portals 132, 134, as shown in FIG. 4. The driver 112 can include an elongate shaft 128 having a handle (not shown) in a proximal portion thereof and having a first mating element 122 in a distal portion thereof. The bone pick 114 can include an elongate shaft 130 having a handle (not shown) in a proximal portion thereof and having a second mating element 124 and a piercing tip 116 in a distal portion thereof. The piercing tip 116 in the illustrated embodiment extends at a fixed 90° angle α1 relative to a longitudinal axis 130L of the bone pick's shaft 130 in at least a distal portion thereof. The piercing tip 116 in the illustrated embodiment also has a longitudinal axis 116L that is coaxial with a longitudinal axis 124L of the second mating element 124. The piercing tip 116 thus can, as in the illustrated embodiment, be centered relative to the second mating element 124, which can help direct force from the driver 112 to the piercing tip 116. The second mating element 124 can, however, be positioned more proximally along the shaft 130 than the piercing tip 116, e.g., closer to the bone pick's handle than the piercing tip 116. The piercing tip 116 could thus be advanced into a tighter region within a body, e.g., a region adjacent an acetabulum, because the region need not include enough space for the second mating element 124 extending from the bone pick 116 or for the first mating element 122 to be in mated engagement with the second mating element 124 within the region.

Figure 6:
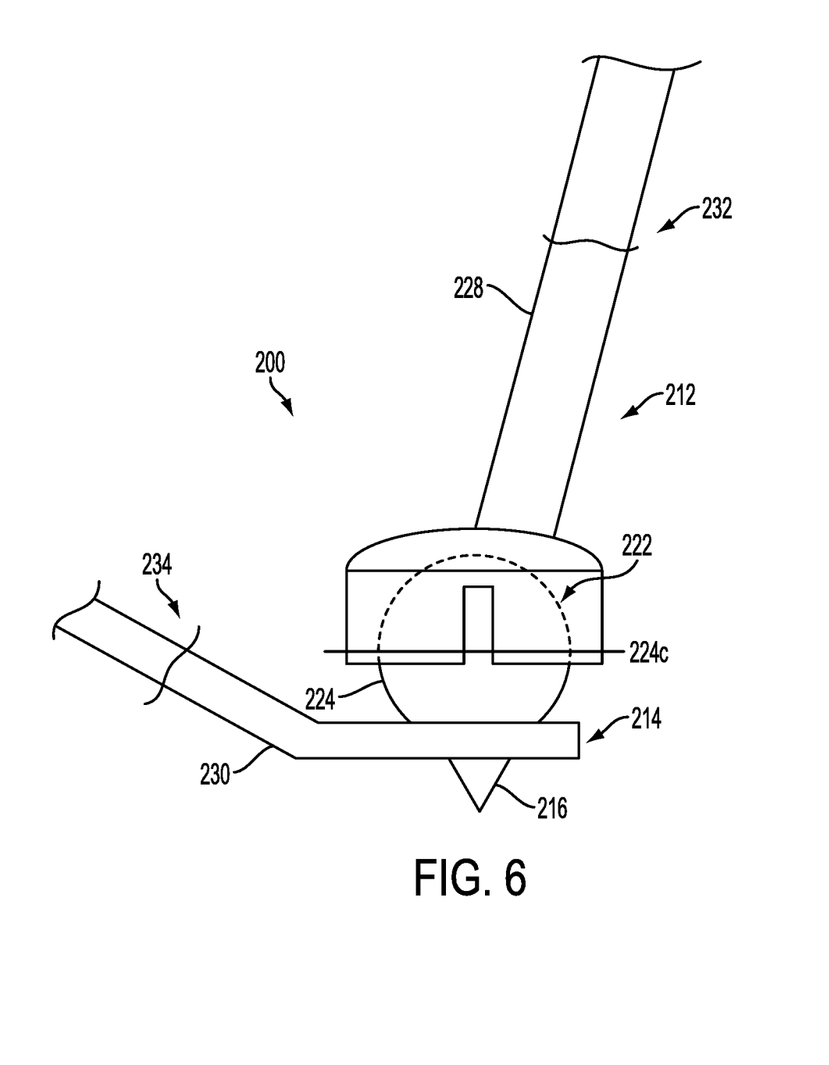
FIG. 6 is a side schematic view of the surgical instrument set of FIG. 5, the driver being advanced through a first access portal in a body, the bone pick being advanced through a second access portal in the body, and the driver and the bone pick being in a mated configuration.

The first and second mating elements 122, 124 can be configured to releasably mate together, as shown in FIG. 4, such that the driver 112 and the bone pick 114 can be angularly adjusted relative to one another. In the illustrated embodiment, the first mating element 122 includes a female element in the form of a socket, and the second mating element 124 includes a male element in the form of a ball having a radius substantially equal to a radius of the socket. The female mating element, e.g., the first mating element 122, can have a depth 122d such that the female mating element has a first maximum width 122w that is smaller than a second maximum width 124w of the male mating element, e.g., the second mating element 124. The first mating element 122 can thus be configured to be positioned entirely proximal to a centerline 124c of the second mating element 124 when the first and second mating elements 122, 124 are mated together, as shown in FIG. 6. The centerline 124c corresponds to the second maximum width 124w. The first mating element 122 thus need not extend around the maximum width 124w of the second mating element 124, e.g., around a central "equatorial" axis of the male element. However, the driver 112 and the bone pick 114 can be angularly adjusted relative to one another such that one portion of the first mating element 122 is positioned proximal to the centerline 124c and another portion of the first mating element 122 is positioned distal to the centerline 124c.

When the driver 112 includes the female mating element 122, as in the illustrated embodiment, the female mating element may have a tendency to accidentally slip relative to the male mating element 124 of the bone pick 114 when releasably mated therewith. To help reduce such accidental slipping, the surgical instrument set 100 can include a retention feature configured to help retain the first and second mating elements 122, 124 together. In other words, the retention feature can help retain the female mating element 122 in releasably mated engagement with the male mating element 124. The retention feature can have a variety of sizes, shapes, and configurations. In the illustrated embodiment, the retention feature includes a tapered distal lip 122r around an exterior perimeter of the driver's distal portion.

Figure 5:
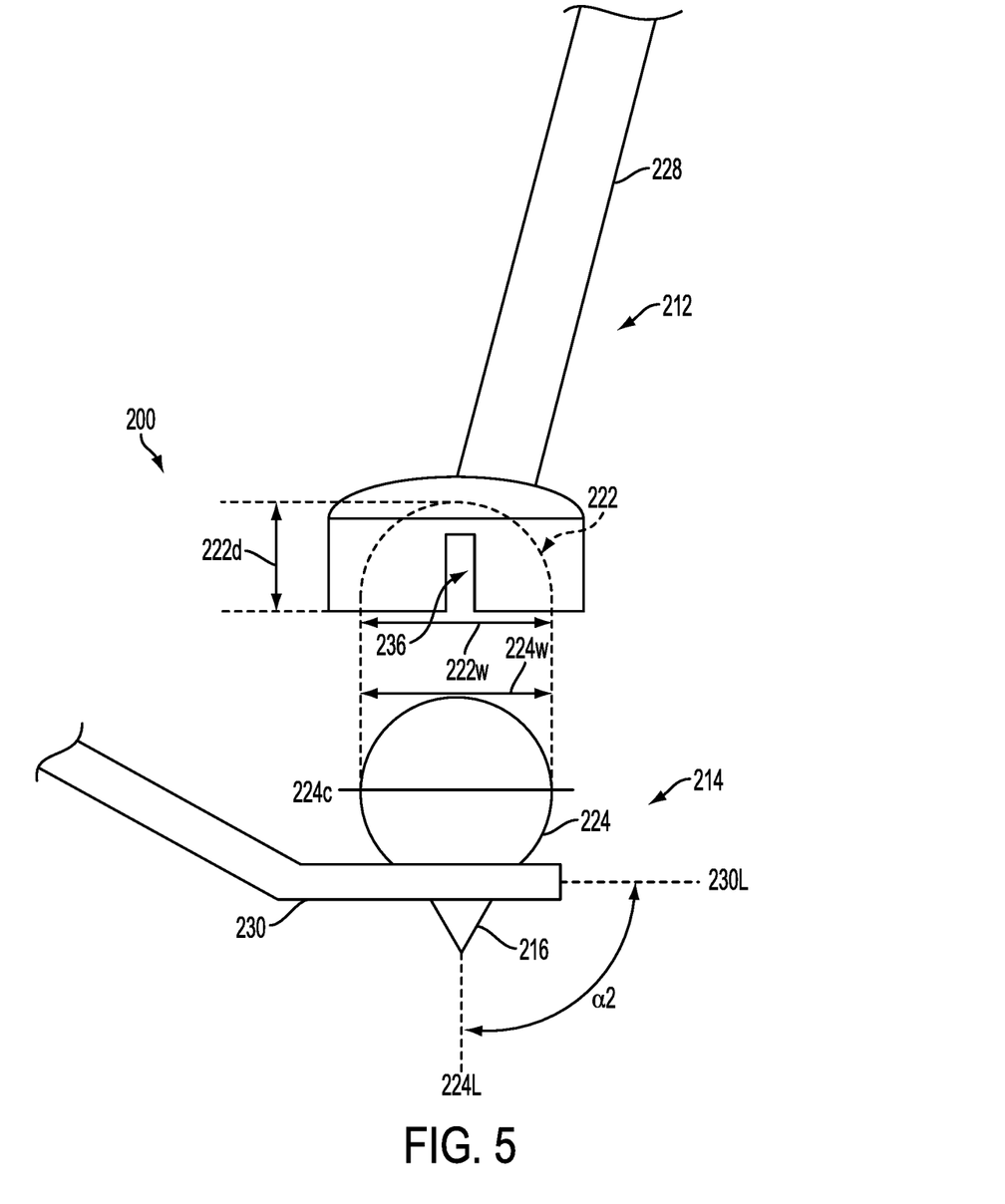
FIG. 5 is a side schematic view of another embodiment of a surgical instrument set including a driver and a bone pick, the driver and the bone pick being in an unmated configuration.

FIGS. 5 and 6 illustrate another embodiment of a surgical instrument set 200 including a driver 212 and a bone pick 214 configured to releasably mate with the driver 212. The driver 212 and the bone pick 214 can be separate elements configured to be advanced into a body through first and second access portals 232, 234, as shown in FIG. 6. The driver 212 can include an elongate shaft 228 having a handle (not shown) in a proximal portion thereof and having a first mating element 222 in a distal portion thereof. The bone pick 214 can include an elongate shaft 230 having a handle (not shown) in a proximal portion thereof and having a second mating element 224 and a piercing tip 216 in a distal portion thereof. The piercing tip 216 in the illustrated embodiment, similar to the piercing tip of FIGS. 3 and 4, extends at a fixed 90° angle α2 relative to a longitudinal axis 230L of the bone pick's shaft 230 in at least a distal portion thereof and coaxial with a longitudinal axis 224L of the second mating element 224.

The first and second mating elements 222, 224 can be configured to releasably mate together, as shown in FIG. 6, such that the driver 212 and the bone pick 214 can be angularly adjusted relative to one another. In the illustrated embodiment, the first mating element 222 includes a female element in the form of a socket, and the second mating element 224 includes a male element in the form of a ball having a radius substantially equal to a radius of the socket. The first and second mating elements 222, 224 can be configured to releasably mate together via snap fit. The snap fit engagement can help reduce chances of the first and second mating elements 222, 224 being released from mating engagement during angular adjustment of the driver 212 and the bone pick 214 and/or during application of a force to the driver 212 that is imparted to the bone pick 214. The female mating element, e.g., the first mating element 222, can have a depth 222d such that the female mating element has a first maximum width 222w that is substantially equal to a second maximum width 224w of the male mating element, e.g., the second mating element 224. The first mating element 222 can thus be configured to be extend around a centerline 224c of the second mating element 224 when the first and second mating elements 222, 224 are mated together.

To facilitate passage of the first mating element 222 across the second mating element's maximum width 224w, e.g., around the centerline 224c, the driver 212 can include at least one slot 236 formed therein. The driver 212 includes two opposed slots 236 in the illustrated embodiment, but the driver 212 can include one or more slots. The at least one slot 236 can be formed in a distal portion of the driver 222 and can be in communication with the female mating element 222, e.g., in communication with the socket. The at least one slot 236 can thus provide "give" in the distal portion of the driver 222, e.g., to allow the distal portion of the driver 212 to expand and contract during passage of the driver 212 across the male mating element's maximum width 224w. The amount of force required to deflect the female mating element 222 radially outward, e.g., during passage of the female mating element 222 around the second mating element's maximum width 224w, can be a relatively small force, e.g., in a range of about 0.25 to 0.75 pounds. The relatively small force can help allow a proximal force applied to driver 212 to disengage the first and second mating elements 222, 224 to not be abrupt, thereby helping to reduce chances of the driver 212 and/or the bone pick 214 from deflecting during disengagement so as to damage adjacent tissue.

A surgical instrument set including a driver and a bone pick can also include a locking mechanism configured to lock the driver and the bone pick in a selected angular orientation relative to one another. The locking mechanism can thus help prevent first and second mating elements of the driver and the bone pick, respectively, from being released from mating engagement during angular adjustment of the driver and the bone pick and/or during application of a force to the driver that is imparted to the bone pick. The locking mechanism can be configured to be movable between a locked position, in which the driver and the bone pick are fixed in the selected angular orientation relative to one another, and an unlocked position, in which the driver and the bone pick are angularly adjustable relative to one another. When the locking mechanism is in the locked position, the instrument set can be handled with one hand, e.g., by holding either of the driver and the bone pick, which can help free hands for other surgical activity. Similarly, a force can be applied to the driver one-handed when the locking mechanism is in the locked position.

Figure 7:
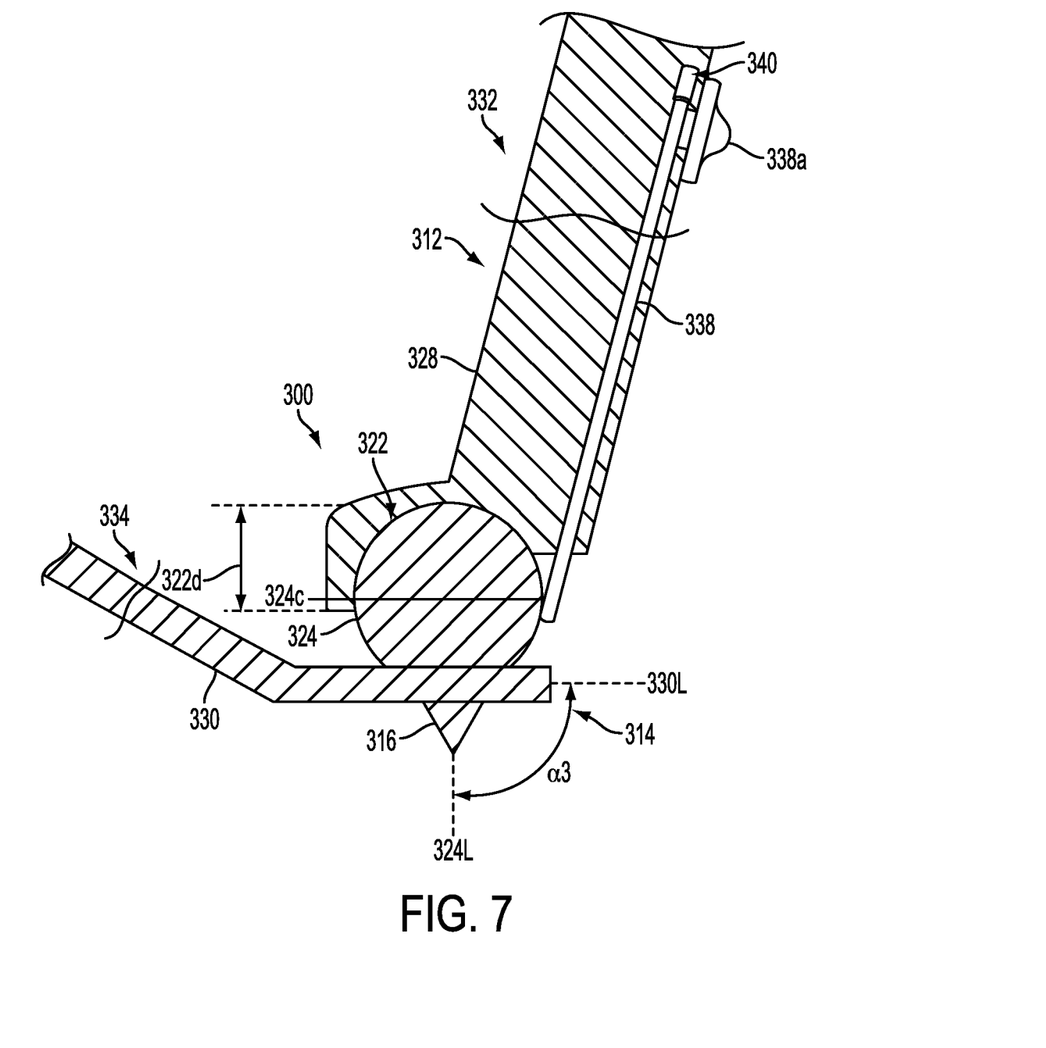
FIG. 7 is a side schematic view of another embodiment of a surgical instrument set including a driver and a bone pick, the driver and the bone pick being in a mated configuration and being fixedly held therein with a locking mechanism of the surgical instrument set.

FIG. 7 illustrates an embodiment of a surgical instrument set 300 including a locking mechanism in the form of a movable lever 338. The surgical instrument set 300 can include a driver 312 and a bone pick 314 configured to releasably mate together and be locked in a selected position relative to one another via the locking mechanism. The driver 312 and the bone pick 314 can be separate elements configured to be advanced into a body through first and second access portals 332, 334 and to releasably mate together via first and second mating elements 322, 324. The driver 312 can include an elongate shaft 328 having a handle (not shown) in a proximal portion thereof and having the first mating element 322 in a distal portion thereof. The bone pick 314 can include an elongate shaft 330 having a handle (not shown) in a proximal portion thereof and having the second mating element 324 and a piercing tip 316 in a distal portion thereof. The piercing tip 316 in the illustrated embodiment, similar to the piercing tip of FIGS. 3 and 4, extends at a fixed 90° angle α3 relative to a longitudinal axis 330L of the bone pick's shaft 330 in at least a distal portion thereof and coaxial with a longitudinal axis 324L of the second mating element 324.

The first and second mating elements 322, 324 can be configured to releasably mate together such that the driver 312 and the bone pick 314 can be angularly adjusted relative to one another. In the illustrated embodiment, the first mating element 322 includes a female element in the form of a socket, and the second mating element 324 includes a male element in the form of a ball having a radius substantially equal to a radius of the socket. The female mating element, e.g., the first mating element 322, can have a depth $322d$ such that the female mating element can extend distally to a centerline $324c$ of the second mating element 324 when the first and second mating elements 322, 324 are mated together.

The lever 338 can extend longitudinally along at least a partial longitudinal length of the driver's shaft 328. The lever 338 can extend through and be movably disposed in a channel 340 extending longitudinally through at least a portion of the driver's shaft 328 as in the illustrated embodiment, but the lever 338 can extend entirely outside the driver's shaft 328, e.g., in a groove formed in an exterior surface of the driver. A distal end of the lever 338 can be configured to be movable within the channel 340 such that the distal end of the lever 338 can be selectively positioned within the channel 340 and outside the channel 340. The lever 338 can be configured to be movable between a locked position, shown in FIG. 7, in which the distal end of the lever 338 is positioned outside the channel 340 and the driver 312 and the bone pick 314 are in a fixed position relative to one another, and an unlocked position in which the distal end of the lever 338 is positioned within the channel 340 and the driver 312 and the bone pick 314 are angularly adjustable relative to one another. In the locked position, a distal end of the lever 338 can be configured to engage the second mating element 324, e.g., abut an exterior surface thereof, when the first mating element 322 engages the second mating element 324. The distal end of the lever 338 can be configured to engage the second mating element 324 opposite to a portion of the first mating element 322 engaging the second mating element 324 below the centerline $324c$ thereof, thereby mimicking the first mating element 222 of the embodiment of FIGS. 5 and 6 in which the first mating element 222 is configured to be extend around the centerline $224c$ of the second mating element 224 when the first and second mating elements 222, 224 are mated together. In the unlocked position, the lever 338 can be in a position proximal to that in the locked position such that the distal end of the lever 338 does not contact the second mating element's exterior surface when the first mating element 322 engages the second mating element 324. In an exemplary embodiment, the lever's distal end is disposed with the channel 340 when the lever 338 is in the unlocked position, which can help prevent the lever's distal end from snagging on tissue or other material at a surgical site and/or during insertion of the driver 312 into a body. The lever 338 can be biased to the unlocked position.

In the illustrated embodiment, the lever 338 can be movable between the unlocked and locked positions by manual movement of a knob $338a$ coupled to a proximal portion of the driver 312 configured to be positioned proximal to the portal 332 through which the driver 312 can be advanced into the body. The knob $338a$ can be configured to slide proximally and distally to move the lever 338 between the locked and unlocked positions. The knob $338a$ can include two detents that signify the locked and unlocked positions. The lever 338 can be movable between the unlocked and locked positions in a variety of other ways, such as by actuation of another mechanical actuator, e.g., push button, switch, etc., or by actuation of an electrical actuator. The instrument set 300 includes a locking mechanism in the form of a manually movable lever 338, but the locking mechanism can have a variety of other configurations, such as an electronically movable lever, a mechanically movable lever, an expandable and compressible distal portion of a driver configured to selectively grip a mating element of a bone pick, etc.

As mentioned above, a bone pick of a surgical instrument set can include a piercing tip configured to extend therefrom at a variable angle. The bone pick can include an adjustment mechanism configured to adjust the angle at which the piercing tip extends from an elongate shaft of the bone pick. The piercing tip can thus be selectively adjusted relative to a bone, which can facilitate penetration of the piercing tip into the bone so as to form a hole therein. The piercing tip being angularly adjusted relative to the elongate shaft can facilitate advancement of the bone pick into a body because the piercing tip can be angled relative to the shaft so as to be at a distal-most end thereof, e.g., to lead the bone pick during advancement thereof. The piercing tip can thus be less likely to scrape against and/or cut into an interior sidewall of an introducer device through which the bone pick can be advanced into the body. After the piercing tip exits the introducer device, the adjustment mechanism can be used to adjust the angle of the piercing tip relative to the bone within the body.

Figure 8:
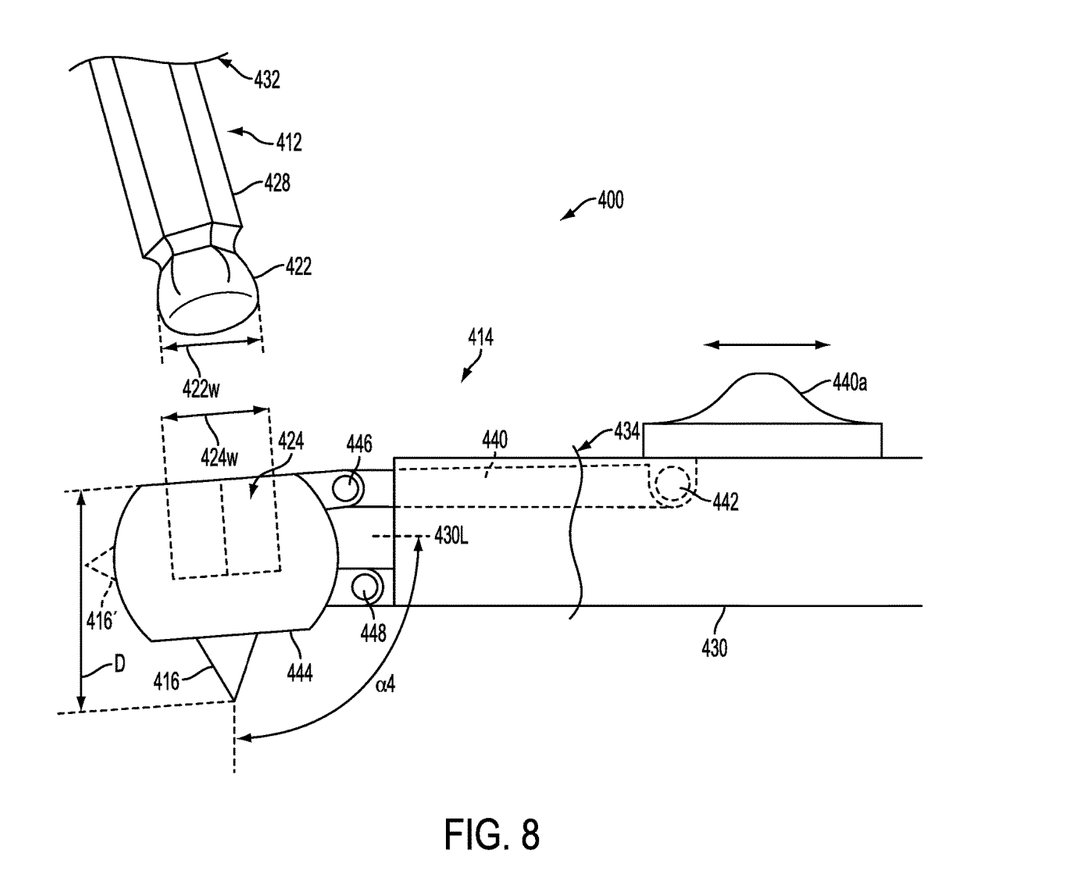
FIG. 8 is a perspective view of one embodiment of a driver of a surgical instrument set and a side schematic view of one embodiment of a bone pick of the surgical instrument set, the driver and the bone pick being in an unmated configuration, and the bone pick having an angularly adjustable distal head.

FIG. 8 illustrates an embodiment of a surgical instrument set 400 including a driver 412 and a bone pick 414 configured to releasably mate with the driver 412. The bone pick 414 can include an elongate shaft 430, a piercing tip 416, and an adjustment mechanism configured to adjust an angle α4 of the piercing tip 416 relative to a longitudinal axis 430L of the elongate shaft 430. The driver 412 and the bone pick 414 can be separate elements configured to be advanced into a body through first and second access portals 432, 434 and to releasably mate together via first and second mating elements 422, 424. The driver 412 can include an elongate shaft 428 having a handle (not shown) in a proximal portion thereof and having the first mating element 422 in a distal portion thereof. The bone pick 414 can include a handle (not shown) in a proximal portion of the shaft 430 and can have the second mating element 424 and the piercing tip 416 in a distal portion thereof.

The first and second mating elements 422, 424 can be configured to releasably mate together such that the driver 412 and the bone pick 414 can be angularly adjusted relative to one another. In the illustrated embodiment, the first mating element 422 includes a male element in the form of a cone-shaped ball, and the second mating element 424 includes a female element in the form of a socket having a radius substantially equal to a radius of the first mating element 422. In the illustrated embodiment, the first mating element 422, 424 have corresponding hexagonal cross-sectional shapes, with the first mating element 422 having a maximum width 422w smaller than a maximum width 424w of the second mating element. The smaller width 422w of the first mating element 422 can allow the driver 412 to be angularly adjusted with respect to the bone pick 414 when the first and second mating elements 422, 424 are mated together. The corresponding hexagonal shapes of the first and second mating elements 422, 424 can provide torsional stability to the angular adjustment. First and second mating elements can have other corresponding cross-sectional shapes, e.g., triangular, octagonal, etc.

The bone pick 414 can include a distal head 444 coupled to a distal end of the shaft 430. The piercing tip 416 can extend from the distal head 444, and the second mating element 424 can be formed in the distal head 444. The second mating element 424 and the piercing tip 416 are on opposed sides of the distal head 444 in the illustrated embodiment, which can allow the first mating element 422 of the driver 412 to be centered over the piercing tip 416 when the first and second mating elements 422, 424 are mated together, which can help direct a force from the driver 412 to the piercing tip 416 with little or no side-to-side movement of the piercing tip 416 when penetrating into bone. In an exemplary embodiment, a depth D of the distal head 444 and the piercing tip 416 can be in a range of about 5 to 7 mm. In another embodiment, a piercing tip 416', shown in phantom in FIG. 8, can extend from the distal head 444 along the longitudinal axis 430L of the elongate shaft 430 of the bone pick 414, e.g., in line with the shaft 430 and coaxial with the shaft's longitudinal axis 430L, at least when the distal head 444 is non-angularly adjusted relative to the shaft 430, which can allow the piercing tip 416' to lead the bone pick's distal advancement into a body and/or can reduce chances of the piercing tip 416' damaging cartilage and/or other tissue during advancement of the piercing tip 416' into the body and during removal of the piercing tip 416' from the body.

The adjustment mechanism can have a variety of sizes, shapes, and configurations. As in the illustrated embodiment, the adjustment mechanism can include a movable lever 440. The lever 440 can extend longitudinally along at least a partial longitudinal length of the bone pick's shaft 430. The lever 440 can extend through and be movably disposed in a channel (not shown) extending longitudinally through at least a portion of the bone pick's shaft 430 as in the illustrated embodiment, but the lever 440 can extend entirely outside the bone pick's shaft 430, e.g., in a groove formed in an exterior surface of the bone pick. A proximal end of the lever 440 can be attached to a knob 440a coupled to a proximal portion of the shaft 430 configured to be positioned proximal to the portal 432 through which the bone pick 414 can be advanced into the body. The proximal end of the lever 440 can be coupled to the knob 440a at a fixed joint 442, e.g., a non-pivoting joint. A distal end of the lever 440 can be coupled to the distal head 444 at a movable joint 446. The distal head 444 can be coupled to the bone pick's shaft 430 at a pivot joint 448.

The knob 440a can be configured to slide proximally and distally to move the lever 440 proximally and distally, respectively, relative to the bone pick's shaft 430. Such proximal and distal movement of the lever 440 can be configured to cause angular movement of the distal head 444 relative to the bone pick's shaft 430, thereby adjusting the angle α4 of the piercing tip 416 relative to the shaft's longitudinal axis 430L. When the lever 440 moves proximally relative to the bone pick's shaft 430, e.g., by manually sliding the knob 440a proximally, the lever 440 can move the movable joint 446 proximally, thereby causing the distal head 444 to pivot about the pivot joint 448 so as to increase the angle α4. Similarly, when the lever 440 moves distally relative to the bone pick's shaft 430, e.g., by manually sliding the knob 440a distally, the lever 440 can move the movable joint 446 distally, thereby causing the distal head 444 to pivot about the pivot joint 448 so as to decrease the angle α4.

As in the illustrated embodiment, the adjustment mechanism can be configured to move between locked and unlocked positions. In the locked position, the adjustment mechanism can be configured to hold the distal head 444, and hence the piercing tip 416, in a fixed position such that the angle α4 is fixed. With the adjustment mechanism in the locked position, a force imparted from the driver 412 to the bone pick 414 when the first and second mating elements 422, 424 are mated together can be less likely to jar the piercing tip 416 in an unintended direction relative to a bone which the piercing tip 416 is piercing. In the unlocked position, the adjustment mechanism can be configured to allow angular adjustment of the distal head 444, and hence the piercing tip 416, such that the angle α4 can be adjusted. The adjustment mechanism can be configured to move between locked and unlocked positions in a variety of ways. In an exemplary embodiment, the knob 440a can include a ratchet that biases the adjustment mechanism to the locked position. The knob 440a can be configured to be pressed down, e.g., pressed radially inward toward the shaft's longitudinal axis 430L, to move the adjustment mechanism from the locked position to the unlocked position such that the knob 440a can be slid proximally and/or distally. When the knob 440a stops being pressed down, the knob 440a can be configured to automatically move radially outward, e.g., away from the shaft's longitudinal axis 430L, to move the adjustment mechanism from the unlocked position to the locked position. As will be appreciated by a person skilled in the art, the adjustment mechanism can be configured to be locked and unlocked in other ways, such as by a push and release button, a movable and lockable switch, etc. A knob of an adjustment mechanism can be configured to be manually held in place to maintain an angle of a piercing tip relative to a bone pick's shaft, e.g., to maintain a piercing tip at a selected angular orientation.

There are numerous methods for using the surgical instrument sets disclosed herein. In use, as mentioned above, the surgical instrument sets disclosed herein can be used in a minimally invasive surgical procedure in which one or more holes are formed in bone, such as in microfracture. The surgical instrument sets disclosed herein can be used in a surgical procedure involving microfracture of a femur at a hip joint, but as will be appreciated by a person skilled in the art, the surgical instrument sets disclosed herein can be used in a variety of surgical procedures at a variety of anatomical locations.

Generally, the patient can first be prepared for the surgery using standard techniques. A driver and a bone pick of a surgical instrument set can be advanced into a body, either simultaneously or sequentially. The driver and the bone pick can be advanced through different access portals, as discussed above, either directly or through an introducer device. The access portals can be formed through skin of the patient specifically for advancement of the driver and the bone pick therethrough, or one or both of the access portals can include previously formed access portals, such as a portal previously formed for advancement of a camera into the body. The relative positioning of the access portals need not be at any predetermined position because first and second mating elements of the driver and the bone pick can allow the driver and the bone pick to be mated together at a plurality of approach angles. The driver and the bone pick can be releasably mated together within the body by mating the first and second mating elements of the driver and the bone pick, respectively. With the driver and the bone pick releasably mated together, an angle of the driver's elongate shaft can be adjusted relative to a piercing tip extending from the bone pick. As discussed above, the angular adjustment can be adjusted with three degrees of freedom. If the instrument set includes a locking mechanism, the locking mechanism can be actuated to lock the driver and the bone pick in a fixed position relative to one another when the first and second mating elements are mated together.

A piercing tip of the bone pick can be positioned adjacent to a bone within the body. If the piercing tip is angularly adjustable relative to a shaft of the bone pick, the angle can be adjusted to position the piercing tip at a desired orientation relative to the bone. The angular adjustment can be performed before and/or after the driver and the bone pick are releasably mated together.

With the driver at a selected angle relative to the piercing tip, a force can be applied to the driver, e.g., by striking, impacting, or otherwise manipulated the driver, such as by striking the driver with a mallet. In an exemplary embodiment, a proximal-most end of the driver can be struck, impacted, or otherwise manipulated, which can facilitate direction of the force toward the piercing tip and the bone. The force can cause the piercing tip to pierce a hole in the bone. The force can be applied one or more times when the piercing tip is at a certain position relative to the bone. Depending on one or more factors such as a hardness of the bone and a desired deepness of the bone, the force can be applied a plurality of times. The piercing tip can be relocated one or more times relative to the bone, and a force can be applied to the driver when the piercing tip is at each of the selected locations such that a plurality of holes are formed in the bone. The driver and the bone pick can remain releasably mated together when the piercing tip is relocated relative to the bone, but if the driver and the bone pick become unmated during relocation of the piercing tip, or at any other time during use, the driver and the bone pick can be re-mated together.

A depth of each of one or more holes formed by the piercing tip can be configured to initiate blood flow including release of fatty droplets. Actual depth of the hole(s) can vary according to patient and location but can generally be in a range of about 2 to 3 mm deep. In some instances, the hole(s) can be equal to or greater than 4 mm, such as if there is a cartilage protrusion or raised area creating space between a top of the cartilage and the bone. If cartilage is not cut back to expose sub-chondral bone, the piercing tip can penetrate even deeper to access the marrow and initiate blood flow through the cartilage and into the sub-chondral bone. A size of a damaged bone area to be perforated with one or more holes is typically in a range of about 1 to 2 cm. A density of a plurality of holes formed in the damaged bone area can be in a range of 4 to 5 holes per square centimeter, with minimum spacing between adjacent holes being in a range of about 2 to 4 mm, e.g., in a range of about 3 to 4 mm, which can allow sufficient bone bridges to remain between adjacent holes so as to provide structural support, e.g., to preserve the integrity and function of the sub-chondral bone plate.

Any bone debris resulting from the bone piercing can be suctioned out of the body by, e.g., a vacuum or suction through a cannulation of the driver. The debris can be suctioned during piercing of the bone and/or after completion of the bone piercing. As mentioned above, any number and any type of surgical instruments can be advanced through a cannulated interior of the driver to access the surgical site, e.g., a scoping device including a camera, a suction device, an irrigation device, etc. The driver thus need not be removed from the body to perform various aspects of the surgical procedure, which can save time during the surgical procedure and can help reduce a number of instruments needed to perform the procedure.

The driver and the bone pick can be released from mating engagement from one another within the body and removed therefrom through their respective access portals. The access portals can then be closed, e.g., sutured closed, or one or more additional surgical instruments can be advanced through one or both of the portals to perform aspects of the surgery.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
   advancing an elongate shaft of a first surgical tool into a body of a patient;
   advancing a second surgical tool into the body of the patient, the second surgical tool including a piercing tip in a distal portion thereof;
   releasably mating the first and second surgical tools together in the body of the patient;
   with the first and second surgical tools releasably mated together, adjusting an angle of the elongate shaft relative to the piercing tip; and
   with the elongate shaft at the selected angle, applying a force to the first surgical tool, thereby causing the piercing tip to pierce a hole in a bone of the patient.

2. The method of claim 1, wherein advancing the first surgical tool into the body of the patient comprises advancing the first surgical tool through a first portal providing access into the body of the patient, and advancing the second surgical tool into the body of the patient comprises advancing the second surgical tool through a second portal providing access into the body of the patient.

3. The method of claim 1, further comprising:
   releasing the first surgical tool from the second surgical tool in the body of the patient; and
   after releasing the first surgical tool from the second surgical tool in the body of the patient, removing the first surgical tool from the body of the patient and removing the second surgical tool from the body of the patient.

4. The method of claim 1, further comprising:
   releasing the first surgical tool from the second surgical tool in the body of the patient.

5. The method of claim 1, wherein adjusting the angle of the elongate shaft relative to the piercing tip comprises adjusting a longitudinal axis of the elongate shaft to be substantially perpendicular to a surface of the bone and to be non-parallel to a longitudinal axis of the piercing tip, the force being applied to a first portion of the surgical tool when the longitudinal axis of the elongate shaft is substantially perpendicular to the surface of the bone and is non-parallel to the longitudinal axis of the piercing tip.

6. The method of claim 1, wherein releasably mating the first and second surgical tools together comprises mating a first mating element on a distal portion of the elongate shaft with a second mating element on a distal portion of the second surgical tool.

* * * * *